United States Patent
Kim et al.

(10) Patent No.: US 11,912,653 B2
(45) Date of Patent: Feb. 27, 2024

(54) NOBLE METAL-TRANSITION METAL COMPLEX CATALYST SUPPORTED ON CARBON-COATED SILICA-ALUMINA SUPPORT, AND PREPARATION METHOD THEREFOR

(71) Applicant: HANWHA SOLUTIONS CORPORATION, Seoul (KR)

(72) Inventors: Jeong Kwon Kim, Seoul (KR); Wan Jae Myeong, Daejeon (KR); Sun Woo Yook, Seongnami-si (KR); Bong Sik Jeon, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 152 days.

(21) Appl. No.: 16/958,430

(22) PCT Filed: Dec. 26, 2018

(86) PCT No.: PCT/KR2018/016688
§ 371 (c)(1),
(2) Date: Jun. 26, 2020

(87) PCT Pub. No.: WO2019/132524
PCT Pub. Date: Jul. 4, 2019

(65) Prior Publication Data
US 2021/0061742 A1  Mar. 4, 2021

(30) Foreign Application Priority Data

Dec. 29, 2017 (KR) .................. 10-2017-0183355

(51) Int. Cl.
*B01J 21/12* (2006.01)
*B01J 21/18* (2006.01)
(Continued)

(52) U.S. Cl.
CPC ............ *C07C 31/276* (2013.01); *B01J 21/12* (2013.01); *B01J 21/18* (2013.01); *B01J 23/626* (2013.01);
(Continued)

(58) Field of Classification Search
CPC ....................................................... B01J 21/12
See application file for complete search history.

(56) References Cited

U.S. PATENT DOCUMENTS

| 9,108,895 B2 | 8/2015 | Liu et al. |
| 2014/0121400 A1 | 5/2014 | Liu et al. |
| 2017/0107164 A1* | 4/2017 | Choi ................. B01J 23/42 |

FOREIGN PATENT DOCUMENTS

| CN | 1911884 A | * | 2/2007 | |
| EP | 681868 A1 | * | 11/1995 | .............. B01J 21/18 |

(Continued)

OTHER PUBLICATIONS

Machine translation of Patent No. EP0681868A1, Nov. 15, 1995; pp. 1-5 (Year: 1995).*
(Continued)

*Primary Examiner* — Medhanit W Bahta
(74) *Attorney, Agent, or Firm* — Sughrue Mion, PLLC

(57) ABSTRACT

Provided are a noble metal-transition metal complex catalyst supported on a carbon-coated silica-alumina support and a preparation method therefor, the catalyst being capable of obtaining a fast reaction rate and catalyst stability, as compared to a conventional catalyst, when cyclohexane dimethanol (CHDM) production is carried out by a cyclohexane dicarboxylic acid (CHDA) hydrogenation reaction in an aqueous solution by using a carbon-coated supported catalyst.

12 Claims, 2 Drawing Sheets

(51) Int. Cl.
    *B01J 23/62*     (2006.01)
    *B01J 37/02*     (2006.01)
    *B01J 37/08*     (2006.01)
    *B01J 37/18*     (2006.01)
    *C07C 29/158*     (2006.01)
    *C07C 31/27*     (2006.01)

(52) U.S. Cl.
    CPC ....... *B01J 37/0205* (2013.01); *B01J 37/0213* (2013.01); *B01J 37/0219* (2013.01); *B01J 37/0228* (2013.01); *B01J 37/0242* (2013.01); *B01J 37/084* (2013.01); *B01J 37/18* (2013.01); *C07C 29/158* (2013.01)

(56) References Cited

FOREIGN PATENT DOCUMENTS

| | | | |
|---|---|---|---|
| JP | 2001 46874 | A | 2/2001 |
| JP | 201554828 | A | 3/2015 |
| JP | 201573960 | A | 4/2015 |
| KR | 1020150079750 | A | 7/2015 |
| WO | 02/083283 | A2 | 10/2002 |
| WO | 2015156582 | A1 | 10/2015 |

OTHER PUBLICATIONS

JP2015073960A, machine translation, Apr. 20, 2015, pp. 1-17 (Year: 2015).*

CN1911884A, machine translation, Feb. 14, 2007, pp. 1-6 (Year: 2007).*

Sigma-Aldrich "1,4-Cyclohexadimethanol" Deposit and available date Jul. 12, 2007 (Year: 2007).*

Hien N. Pham et al., "Carbon Overcoating of Supported Metal Catalysts for Improved Hydrothermal Stability", American Chemical Society, vol. 5, 2015, pp. 4546-4555 (11 pages total).

Yoshinori Hara et al., "The drastic effect of platinum on carbon-supported ruthenium-tin catalysts used for hydrogenation reactions of carboxylic acids", Applied Catalysis A: General, vol. 239, 2003, pp. 181-195 (16 pages total).

Takashi Fujikawa et al., "Aromatic hydrogenation of distillates over $SiO_2$-$Al_2O_3$-supported noble metal catalysts", Applied Catalysis A: General, vol. 192, 2000, pp. 253-261 (10 pages total).

Laura Roldán et al., "The formation of a hydrothermal carbon coating on graphite microfiber felts for using as structured acid catalyst", Carbon, vol. 50, 2012, pp. 1363-1372 (11 pages total).

Amanda Lynn Staker, "Carbon Coating for Improved Hydrothermal Stability of Silica Supports", B.A., ACS Chemistry Gustavus Adolphus College, 2009, (86 pages total).

International Searching Authority, International Search Report dated Apr. 3, 2019, in International Application No. PCT/KR2018/016688.

Lun-Gang Chen et al., "Research Progress on Reaction Mechanism and Catalysts for Hydrogenation of Carboxylic Acids", Journal of Molecular Catalysis(China), vol. 31, No. 3, Jun. 2017, pp. 267-276 (10 total pages).

* cited by examiner

NOBLE METAL-TRANSITION METAL COMPLEX CATALYST SUPPORTED ON CARBON-COATED SILICA-ALUMINA SUPPORT, AND PREPARATION METHOD THEREFOR

CROSS REFERENCE TO RELATED APPLICATIONS

This application is a National Stage of International Application No. PCT/KR2018/016688 filed Dec. 26, 2018, claiming priority based on Korean Patent Application No. 10-2017-0183355 filed Dec. 29, 2017.

TECHNICAL FIELD

The present invention relates to a noble metal-transition metal complex catalyst supported on a carbon-coated silica-alumina carrier (support) and a preparation method therefor, and more particularly, to a noble metal-transition metal complex catalyst supported on a carbon-coated silica-alumina carrier and a preparation method therefor, the catalyst being capable of obtaining a fast reaction rate and catalyst stability, as compared to a conventional catalyst, when cyclohexane dimethanol (CHDM) production is carried out by a cyclohexane dicarboxylic acid (CHDA) hydrogenation reaction in an aqueous solution by using a carbon-coated supported catalyst.

BACKGROUND ART

Cyclohexane dimethanol (CHDM, 1,4-cyclohexanedimethanol) is the basic raw material for the preparation of polyester or polyamide resins. CHDM is commercially prepared in Asia by SK NJC, which is a joint-venture firm established by SK Chemicals, Mitsubishi Corporation, and Shin Nippon Rika. Indorama [old name: Eastman] is dominating the entire markets all over the world. In the CHDM market, a demand for high value-added polyester resins is increasing and is expected to increase in the future. Thus, stable supply and demand is required. Currently, Indorama produces 100 KTA of CHDM and SK NJC produces 20 KTA of CHDM. It is known that SK NJC plans to increase the production to 60 KTA by 2018. It is known that one production line has recently been expanded in two existing production lines.

According to the known documents, there are three methods for preparing a CHDM using a purified terephthalic acid (RTA). According to a first method, salt is produced by ionizing PTA of Sumitomo Seika Chemicals Co., Ltd. with NaOH in an aqueous solution to increase PTA solubility and a hydrogenation reaction is performed. This synthesis method has an advantage that lowers a hydrogenation reaction temperature as PTA solubility increases at a low temperature (40° C. to 130° C.). However, after the reaction, a process of neutralizing with HCl to recover Na$^+$ ions is required. After the residual Na$^+$ salt reacts, it affects PETG polymerization. Also, a brine solution containing NaCl incurs excessive wastewater treatment costs. This adversely affects the cost reduction of the production process. A second method is a preparation method used by Indorama and SK NJC. Dimethyl terephthalate (DMT) is prepared by esterifying PTA and CHDM is prepared through dimethyl cyclohexane dicarboxylate (DMCD). Since this process uses a Cu-based or Cr-based catalyst when preparing CHDM from DMCD, it is relatively inexpensive in terms of catalyst price. However, since this process is a three-step preparation process (PTA DMT→DMCD CHDM), it is disadvantageous in terms of process. In addition, since different solvents are used in two processes, a large amount of wastewater is generated and DMT, which is more expensive than PTA, is used as the raw material.

On the other hand, a third method is a process of preparing CHDM from PTA through CHDA. Since ruthenium, which is a noble metal, is used as an active metal in a CHDA hydrogenation reaction, it is disadvantageous in terms of catalyst price. However, since the final product CHDM can be obtained through the two-step process (PTA CHDA CHDM), it is determined that this process is advantageous in terms of cost reduction if the product cost is reduced through a reduction in process steps and the competitiveness of process technology is secured.

The two-step process of preparing a CHDA and a CHDM through a PTA has a higher difficulty in a two-step reaction, which is a conversion reaction for converting a di-carboxylic acid into alcohol by hydrodeoxygenation, than a one-step reaction for saturating an aromatic ring of a TPA. Thus, the two-step process acts as a huddle in a commercialization stage. Therefore, it is urgent to develop a high efficiency/long life catalyst suitable for a CHDA hydrogenation process, which is a two-step reaction.

DESCRIPTION OF EMBODIMENTS

Technical Problem

The present invention aims to solve the above-described problems of the related art and the technical problems requested from the past.

An object of the present invention is to provide a noble metal-transition metal complex catalyst supported on a carbon-coated silica-alumina carrier, capable of maintaining high activity and catalytic reaction stability when diol is prepared from a dicarboxylic acid using the noble metal-transition metal complex catalyst supported on carbon-coated silica-alumina ($SiO_2$—$Al_2O_3$), and a preparation method therefor.

Solution to Problem

In order to achieve the objects, the present invention provides a noble metal-transition metal complex catalyst supported on a carbon-coated carrier.

The catalyst is a complex catalyst in which noble metal-transition metal is supported on a carbon-coated silica-alumina carrier.

40 parts by weight to 95 parts by weight of alumina ($Al_2O_3$) and 5 parts by weight to 60 parts by weight of silica ($SiO_2$) may be included based on 100 parts by weight of the carrier; and 1 part by weight to 20 parts by weight of the noble metal and the transition metal may be included based on 100 parts by weight of the carbon-coated silica-alumina carrier.

In one preferred embodiment of the present invention, the noble metal may include one or more selected from the group consisting of palladium (Pd), rhodium (Rh), ruthenium (Ru), and platinum (Pt).

In one preferred embodiment of the present invention, an amount of the noble metal may be in a range of 1 part by weight to 10 parts by weight based on 100 parts by weight of the carrier.

In one preferred embodiment of the present invention, the transition metal may include one or more selected from the group consisting of tin (Sn), iron (Fe), rhenium (Re), and gallium (Ga).

In one preferred embodiment of the present invention, an amount of the transition metal may be in a range of 1 part by weight to 10 parts by weight based on 100 parts by weight of the carrier.

In one preferred embodiment of the present invention, a noble metal precursor and a transition metal precursor may be supported on the carrier at the same molar ratio.

In one preferred embodiment of the present invention, the carbon may be coated on the surface of the silica-alumina through a carbonization process.

The present invention provides a hydrogenation method for hydrogenating a dicarboxylic acid group using the catalyst and a cyclohexane dimethanol (CHDM) prepared by performing a hydrogenation reaction of a cyclohexane dicarboxylic acid (CHDA) on the catalyst.

In one preferred embodiment of the present invention, the dicarboxylic acid may be one selected from the group consisting of an oxalic acid, a malonic acid, a succinic acid, a glutaric acid, an adipic acid, a pimelic acid, a suberic acid, an azelaic acid, a sebacic acid, a malic acid, an aspartic acid, a glutamic acid, a phthalic acid, an isopthalic acid, a terephthalic acid, and a cyclohexane dicarboxylic acid.

The present invention provides a method for preparing a noble metal-transition metal complex catalyst supported on a carbon-coated silica-alumina carrier, the method including:

(a) preparing a complex by dissolving a boric acid in an aqueous carbon precursor solution and supporting the resultant mixture on silica-alumina ($SiO_2$—$Al_2O_3$);
(b) carbonizing the complex;
(c) supporting a noble metal-transition metal on a carbon-coated silica-alumina ($SiO_2$—$Al_2O_3$) carrier; and
(d) reducing a noble metal-transition metal oxide supported on the silica-alumina ($SiO_2$—$Al_2O_3$) carrier with hydrogen.

In one preferred embodiment of the present invention, in the step (a), the carbon precursor and the boric acid may be added at a weight ratio of 1:0.005 to 1:0.1.

In one preferred embodiment of the present invention, in the step (a), the complex may be prepared by being supported on the carrier by incipient-wetness impregnation.

In one preferred embodiment of the present invention, the carbonization process may be performed in a temperature range of 300° C. to 700° C. in a nitrogen atmosphere.

In one preferred embodiment of the present invention, in the step (c), the noble metal and the transition metal may be supported in 1 part by weight to 20 parts by weight based on 100 parts by weight of the carrier.

In one preferred embodiment of the present invention, in the step (d), the reduction process may be performed in a temperature range of 400° C. to 600° C.

Advantageous Effects of Disclosure

As described above, a noble metal-transition metal catalyst supported on a carbon-coated silica-alumina carrier and a preparation method therefor have an effect that can maintain high activity and catalytic reaction stability when diol is prepared from a dicarboxylic acid using a noble metal-transition metal catalyst supported on carbon-coated silica-alumina ($SiO_2$—$Al_2O_3$).

BEST MODE

Figure 1:
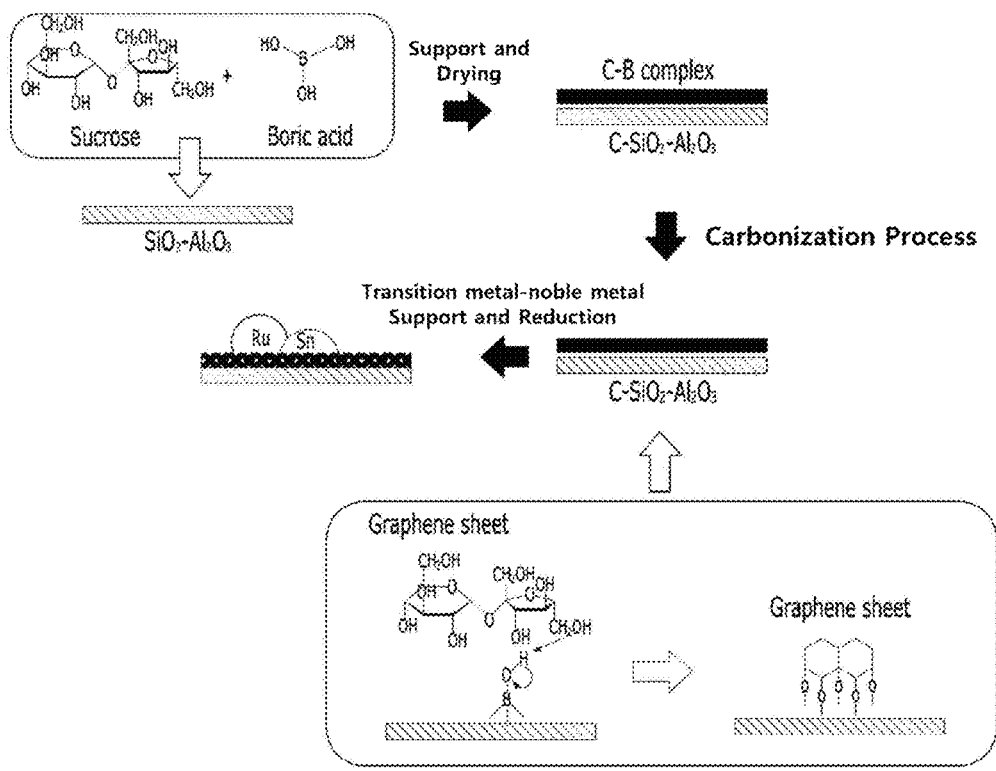
FIG. 1 is a schematic diagram of a preparation process in which a noble metal-transition metal is supported on a carbon-coated silica-alumina carrier, according to an embodiment of the present invention.

The present invention will be described with reference to specific embodiments and the accompanying drawings. The embodiments will be described in detail in such a manner that the present invention may be carried out by those of ordinary skill in the art. It should be understood that various embodiments of the present invention are different, but need not be mutually exclusive. For example, certain shapes, structures, and features described herein may be implemented in other embodiments without departing from the spirit and scope of the present invention in connection with one embodiment.

Therefore, the following detailed description is not to be taken in a limiting sense, and the scope of the present invention is to be limited only by the appended claims and the entire scope of equivalents thereof, if properly explained.

In addition, unless otherwise specified in the present specification, the term "substitution" or "substituted" means that one or more hydrogen atoms in the functional groups of the present invention are substituted with one or more substituents selected from the group consisting of a halogen atom (—F, —Cl, —Br, or —I), a hydroxy group, a nitro group, a cyano group, an amino group, an amidino group, a hydrazine group, a hydrazone group, a carboxyl group, an ester group, a ketone group, a substituted or unsubstituted alkyl group, a substituted or unsubstituted alicyclic organic group, a substituted or unsubstituted aryl group, a substituted or unsubstituted alkenyl group, a substituted or unsubstituted alkynyl group, a substituted or unsubstituted heteroaryl group, and a substituted or unsubstituted heterocyclic group. These substituents may be linked to each other to form a ring.

In the present invention, unless otherwise specified, the term "substituted" means that a hydrogen atom is substituted with a substituent such as a halogen atom, a $C_1$-$C_{20}$ hydrocarbon group, a $C_1$-$C_{20}$ alkoxy group, and a $C_6$-$C_{20}$ aryloxy group.

In addition, unless otherwise specified, the term "hydrocarbon group" refers to a linear, branched, or cyclic saturated or unsaturated hydrocarbon group. The alkyl group, the alkenyl group, the alkynyl group, and the like may be linear, branched, or cyclic.

In addition, unless otherwise specified in the present specification, the term "alkyl group" refers to a $C_1$-$C_{30}$ alkyl group and the term "aryl group" refers to a $C_6$-$C_{30}$ aryl group. In the present specification, the term "heterocyclic group" refers to a group in which one to three heteroatoms selected from the group consisting of O, S, N, P, Si, and any combination thereof are contained in one ring. Examples of the heterocyclic group may include pyridine, thiophene, and pyrazine, but the present invention is not limited thereto.

In the detailed description of the present invention, the term "dicarboxylic acid" refers to an organic acid having two carboxylic acid functional groups in one molecule. For example, the molecular formula of the dicarboxylic acid is HOOC—R—COOH. In the present invention, R is preferably an alkyl group or an aryl group.

Hereinafter, embodiments of the present invention will be described with reference to the accompanying drawings, so that those of ordinary skill in the art can easily carry out the present invention.

As described above, the conventional cyclohexane dicarboxylic acid (CHDA) hydrogenation reaction technology has a limitation in the preparation of the cyclohexane dimethanol (CHDM) using a catalyst having a high reaction activity and hydrothermal stability, as compared to a conventional catalyst, while using an inexpensive carrier.

The present invention solves the above problems by providing a noble metal-transition metal catalyst in which a noble metal-transition metal is supported on a carbon-coated silica-alumina carrier, wherein 40 parts by weight to 95 parts by weight of alumina ($Al_2O_3$) and 5 parts by weight to 60 parts by weight of silica ($SiO_2$) are included based on 100 parts by weight of the carrier, and 1 part by weight to 20 parts by weight of the noble metal and the transition metal are included based on 100 parts by weight of the carbon-coated silica-alumina carrier.

Since the carrier can act as a catalyst poison under the influence of acid, metal oxides such as silica, alumina, zirconium oxide, and titanium dioxide, complex oxides such as silica-alumina, acidic activated carbon, zeolite, and the like may be used.

Generally, in the case of the alumina carrier, there is a disadvantage that a structure of gamma alumina may be changed to a boehmite structure under hydrothermal reaction conditions. Therefore, as a method for increasing the hydrothermal stability of alumina, various methods of performing pretreatment with second other components have been introduced. Also, when silica is used as a carrier, since a bond between cobalt and the carrier is strong as compared to an alumina carrier, a decrease in the reducibility of the cobalt metal in a reduction process and thus a decrease in its activity are observed. As a method for overcoming this problem, a method of pre-treating a silica surface using a metal such as zirconium has been introduced as a conventional technique.

In the carrier of the present invention, since two components of $Al_2O_3$ and $SiO_2$ are present at the same time, the disadvantages when the alumina component and the silica component are used alone is improved. A solution including a carbon precursor is supported on the alumina-silica carrier through incipient-wetness impregnation to form a complex, and the complex is used as a catalyst for a dicarboxylic acid hydrogenation reaction through carbonization.

Hereinafter, the composition of the noble metal-transition metal catalyst supported on the carbon-coated carrier will be described in more detail.

According to the present invention, an amount of the alumina component may be preferably in a range of 40 parts by weight to 95 parts by weight based on 100 parts by weight of the entire carrier. The amount of the alumina component may be in a range of preferably 55 parts by weight to 85 parts by weight, and more preferably 80 parts by weight to 85 parts by weight. In this case, when the amount of the alumina component is less than 40 parts by weight, a high acid point of the silica-alumina carrier may cause by-products to be excessively generated by hydrocracking during the reaction. When the amount of the alumina component exceeds 95 parts by weight, a problem may occur in hydrothermal stability of alumina. Therefore, the above range is preferable.

An amount of the silica component may be preferably in a range of 5 parts by weight to 60 parts by weight based on 100 parts by weight of the entire carrier. The amount of the silica component may be in a range of preferably 5 parts by weight to 35 parts by weight, and more preferably 5 parts by weight to 10 parts by weight. In this case, when the amount of the silica component is less than 5 parts by weight, a problem may occur in hydrothermal stability of alumina. When the amount of the silica component exceeds 50 parts by weight, a high acid point of the silica-alumina carrier may cause hydrocracking. Therefore, the above range is preferable.

The noble metal may include one or more selected from the group consisting of palladium (Pd), rhodium (Rh), ruthenium (Ru), and platinum (Pt). According to the present invention, an amount of the noble metal may be in a range of 1 part by weight to 20 parts by weight based on 100 parts by weight of the carbon-coated silica-alumina carrier. The amount of the noble metal may be in a range of preferably 1 part by weight to 10 parts by weight, and more preferably 3 parts by weight to 8 parts by weight. In this case, when the amount of the noble metal is less than 1 part by weight, the conversion efficiency is low and thus the production efficiency is reduced. When the amount of the noble metal exceeds 10 parts by weight, additional cost may be incurred in a process due to a high catalyst price and low selectivity of the target product. Therefore, the above range is preferable.

The transition metal may include one or more selected from the group consisting of tin (Sn), iron (Fe), rhenium (Re), and gallium (Ga). According to the present invention, an amount of the transition metal may be in a range of 1 part by weight to 20 parts by weight based on 100 parts by weight of the carbon-coated silica-alumina carrier. The amount of the transition metal may be in a range of preferably 1 part by weight to 10 parts by weight, and more preferably 3 parts by weight to 8 parts by weight. In this case, when the amount of the transition metal is less than 1 part by weight, the conversion efficiency of the reaction is lowered or the selectivity of the target product is lowered. Thus, excessive separation and recovery costs in the process may be used. When the amount of the transition metal exceeds 10 parts by weight, additional processes may be required due to the occurrence of many by-products.

The present invention provides a hydrogenation method using the above-described catalyst, and in a specific example, a cyclohexane dimethanol (CHDM) may be prepared through a cyclohexane dicarboxylic acid (CHDA) hydrogenation reaction on a catalyst.

Hereinafter, a method for preparing a noble metal-transition metal complex catalyst supported on a carbon-coated carrier including the above-described composition will be described.

The present invention provides a method for preparing a noble metal-transition metal complex catalyst supported on a carbon-coated carrier. Specifically, the method includes: preparing a complex by dissolving a boric acid in an aqueous carbon precursor solution and supporting the resultant mixture on silica-alumina ($SiO_2$—$Al_2O_3$); carbonizing the complex; supporting a noble metal-transition metal on a carbon-coated silica-alumina ($SiO_2$—$Al_2O_3$) carrier; and reducing a noble metal-transition metal oxide supported on the silica-alumina ($SiO_2$—$Al_2O_3$) carrier with hydrogen.

Referring to FIG. 1, a boric acid is dissolved in an aqueous carbon precursor solution and supported on a silica-alumina ($SiO_2$—$Al_2O_3$) to prepare a complex. A carbonization process is performed by introducing the complex at a temperature of 500° C. in a nitrogen atmosphere. Then, the noble metal precursor and the transition metal precursor having the above-described content ratio are supported on the carbon-coated silica-alumina ($SiO_2$—$Al_2O_3$) carrier by co-impregnation, such that the noble metal-transition metal oxide is reduced with hydrogen. In this manner, a catalyst including the noble metal-transition metal in the carbon-coated carrier is prepared.

According to the present invention, the carbon precursor and the boric acid added to the aqueous carbon precursor solution may be added at a weight ratio of 1:0.005 to 1:0.1. The carbon precursor and the boric acid may be added at a weight ratio of preferably 1:0.007 to 1:0.07, and more preferably 1:0.01 to 1:0.05. In this case, when the weight ratio of the boric acid is less than 0.005, the electronic charge density of the active metal decreases and the amount of hydrogen adsorption decreases, resulting in a decrease in the catalytic reaction activity. When the weight ratio of the boric acid exceeds 0.1, an excessive amount of the boric acid is dissolved in the target product and a problem may occur in product quality. Therefore, the above range is preferable.

Hereinafter, preferred examples are presented so as to help the understanding of the present invention. However, the following examples are for illustrative purposes only and the present invention is not limited by the following examples.

EXAMPLES

<Example 1> Preparation of Complex by Coating Carbon on $SiO_2$—$Al_2O_3$

First, 9.75 g of sucrose (Aldrich) was added to 10 ml of distilled water and stirred using a magnetic stirrer. After the sucrose was completely dissolved in the distilled water, 0.2 g of boric acid (Aldrich) was added and dissolved in an aqueous sucrose solution for 2 hours. Subsequently, the solution was supported on an $SiO_2$—$Al_2O_3$ carrier through incipient-wetness impregnation.

The prepared complex carbonized the coated sucrose through a carbonization process. The carbonization was performed at 300° C. for 3 hours. At this time, the sucrose was attached to the surface of $SiO_2$—$Al_2O_3$ through dehydration between the hydroxyl group and the sucrose on the surface of $SiO_2$—$Al_2O_3$. Subsequently, it was confirmed that the sucrose attached to the surface was changed to a polycyclic aromatic carbon sheet after the carbonization process was performed at 500° C. for 3 hours. The carbonization process was performed under a condition that nitrogen flowed at 100 cc/min and a ramping rate was 5° C./min.

<Example 2> Noble Metal Ruthenium-Tin was Supported on C—$SiO_2$-$Al_2O_3$Carrier In order to support ruthenium and tin on the C—$SiO_2$—$Al_2O_3$ carrier, a ruthenium precursor ($RuCl_3$, Kojima) and a tin precursor ($SnCl_2$, Aldrich) were dissolved in a distilled water solution and supported through co-impregnation of supporting the two precursors at a time. In the catalyst, 5 parts by weight of ruthenium based on 100 parts by weight of the C—$SiO_2$—$Al_2O_3$ carrier was supported. At this time, the amount of the tin was supported in the same number of moles as ruthenium and reduced at 500° C. for 3 hours (100 cc/min $H_2$:30/$N_2$:70), and this was used as a catalyst for a dicarboxylic acid hydrogenation reaction.

<Example 3> CHDM Production Reaction Through Conversion of CHDA Using Ru—Sn/C—$SiO_2$—$Al_2O_3$Catalyst A ruthenium-tin catalyst (Ru—Sn/C—$SiO_2$—$Al_2O_3$) supported on C—$SiO_2$—$Al_2O_3$ was applied to a hydroconversion reaction of dicarboxylic acid into diol. In the hydroconversion reaction, a cyclohexanedicarboxylic acid (CHDA) represented by a dicarboxylic acid was selected and converted into cyclohexanedimethanol (CHDM) through selective hydrogenation. This reaction was performed in a liquid phase reaction, and an acid-resistant titania batch reactor was used. For the reaction, a high-temperature and high-pressure autoclave reactor was filled with a CHDA as a reactant and a catalyst at a weight ratio of 3.75:1 and was filled with distilled water as a reaction solvent. At this time, the amount of the reactant relative to the reaction solvent was fixed to 7 wt %. Subsequently, the reactor was pressurized to a reaction pressure by using hydrogen, such that whether the reactor leaked was checked through a hydrogen detector. Oxygen inside the reactor was completely removed by depressurization and purging. Finally, the pressure inside the reactor was set to 10 bar, the reactor was heated to the reaction temperature, and the reactor was pressurized to the reaction pressure of the hydrogen atmosphere. Then, the reaction was performed for 6 hours. The reaction was performed at 90° C. and 90 bar for 6 hours, and the stirring was maintained at a speed of 1,000 rpm by using an overhead impeller. After the reaction, the reactor was cooled to room temperature and decompressed, such that the catalyst and the liquid product were separated by filtration and analyzed by gas chromatography with an HP-1 column. The conversion rate, selectivity, and yield of a CHDM, a CHMA, ester, and the like generated according to the CHDA conversion were calculated using Equations 1 to 3:

$$\text{Conversion of } CHDA\,(\%) = \frac{\text{Mole of } CHDA \text{ Reacted}}{\text{Mole of } CHDA \text{ in the Feed}} \times 100 \quad <\text{Equation 1}>$$

$$\text{Selectivity for } CHDM(\%) = \frac{\text{Mole of } CHDM \text{ formed}}{\text{Mole of } CHDA \text{ reacted}} \quad <\text{Equation 2}>$$

$$\text{Yield for } CHDM(\%) = (\text{Conversion of } CHDA) \times (\text{Selectivity for } CHDM) \quad <\text{Equation 3}>$$

Figure 2:
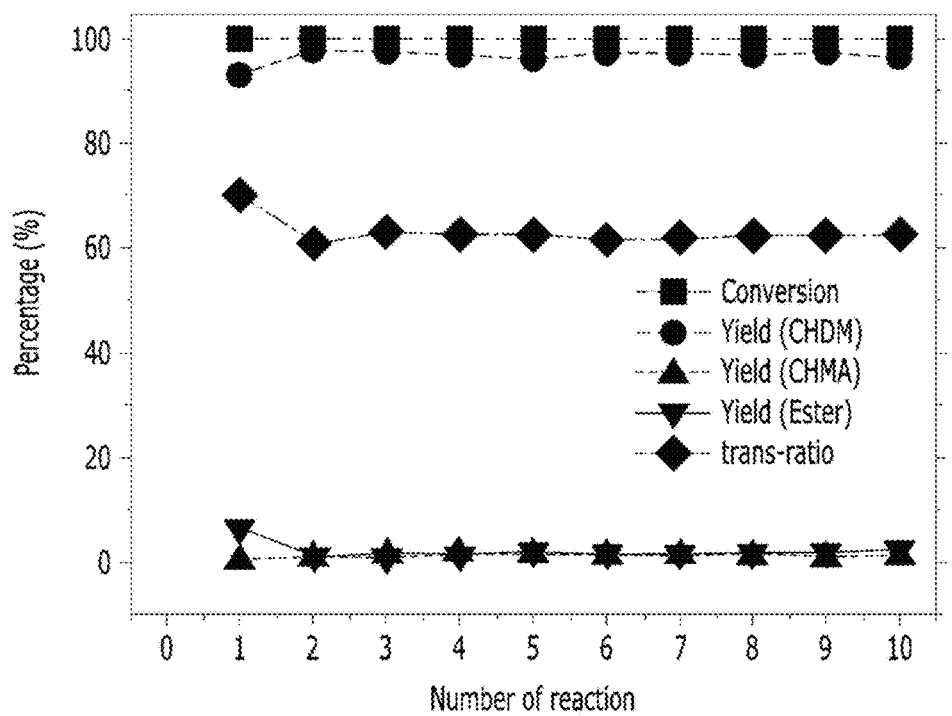
FIG. 2 is a graph showing the results of a CHDM production reaction using a catalyst in which a noble metal-transition metal is supported on a carbon-coated silica-alumina carrier, according to an embodiment of the present invention.

In this regard, the long-term stability test was performed while the reaction for evaluating the performance of the Ru—Sn/C—$SiO_2$—$Al_2O_3$ catalyst in producing the CHDM through the CHDA hydrogenation reaction was performed a total of 10 times, and the results thereof are shown in FIG. 2. The reaction was performed for 6 hours in the hydrogen atmosphere at 230° C. and 90 bar.

It was confirmed that the conversion rate of the CHDA was 99% or more in all the ten reaction results, and the yield for the CHDM was 93 to 97%.

Comparative Examples

<Comparative Example 1> Preparation of Ru—Sn/SiO$_2$—Al$_2$O$_3$ Catalyst and CHDA Hydrogenation Reaction Experiment A Ru—Sn/SiO$_2$—Al$_2$O$_3$ catalyst was prepared in the same manner as in Example 1, except for the process of coating carbon.

Specifically, 5 parts by weight of ruthenium based on 100 parts by weight of a SiO$_2$—Al$_2$O$_3$ carrier was supported. At this time, the amount of the tin was supported in the same number of moles as ruthenium and reduced at 500° C. for 3 hours (100 cc/min H$_2$:30/N$_2$:70), and this was used as a catalyst for a dicarboxylic acid hydrogenation reaction.

Figure 3:
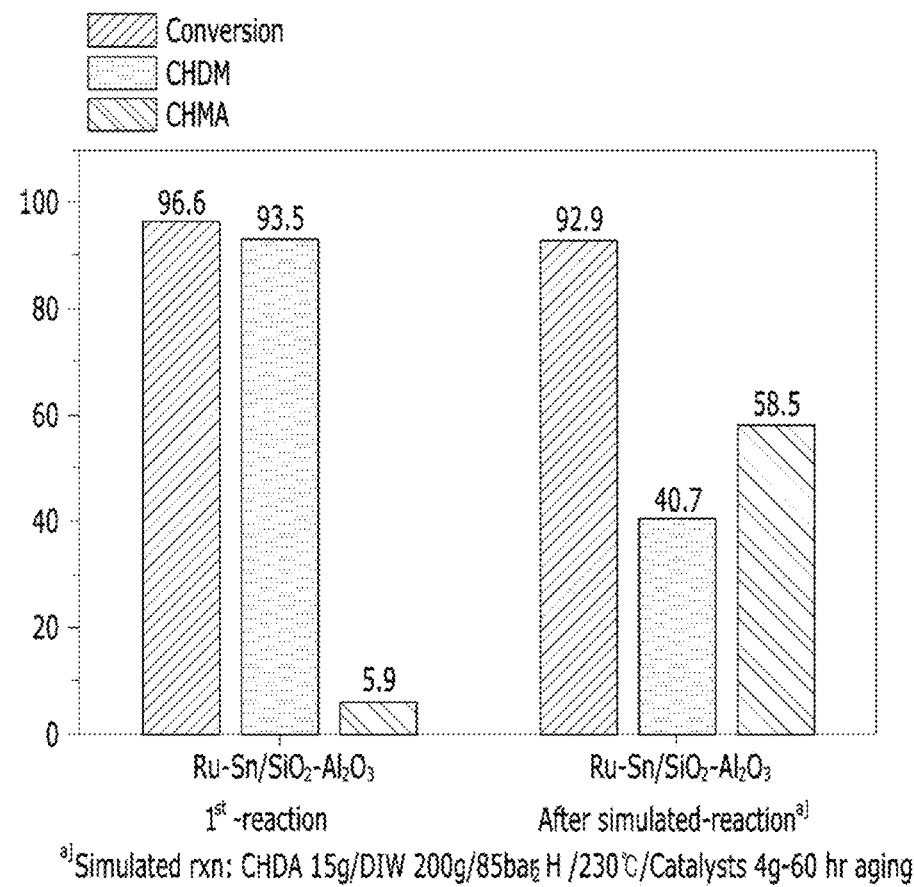
FIG. 3 is a graph showing the results of a CHDM production reaction using a catalyst in which a noble metal-transition metal is supported on a carbon-uncoated silica-alumina carrier, according to an embodiment of the present invention.

In this regard, in order to confirm the hydrothermal stability of the Ru—Sn/SiO$_2$—Al$_2$O$_3$ catalyst, hydrothermal treatment was performed on the catalyst at reaction conditions for 60 hours, and the results of comparison with initial reaction activity are shown in FIG. 3.

As a result, it was confirmed that the Ru—Sn/SiO$_2$—Al$_2$O$_3$ catalyst exhibited excellent initial activity like the Ru—Sn/C—SiO$_2$—Al$_2$O$_3$ catalyst, but the reaction activity was greatly reduced after exposure to the hydrothermal conditions for 60 hours.

<Comparative Example 2> Preparation of Ru—Sn/C-Al$_2$O$_3$ Catalyst and CHDA Hydrogenation Reaction Experiment A Ru—Sn/C—Al$_2$O$_3$ catalyst was prepared by using an Al$_2$O$_3$ carrier, instead of a SiO$_2$—Al$_2$O$_3$ carrier, so as to verify the performance and durability of the Ru—Sn/C—SiO$_2$—Al$_2$O$_3$ catalyst. A catalyst preparation method was performed in the same manner as in the method for preparing the C—SiO$_2$—Al$_2$O$_3$ carrier in Example 1, except that SiO$_2$—Al$_2$O$_3$ was changed to Al$_2$O$_3$.

Specifically, 9.75 g of sucrose (Aldrich) was added to 10 ml of distilled water and stirred using a magnetic stirrer. After the sucrose was completely dissolved in the distilled water, 0.2 g of boric acid (Aldrich) was added and dissolved in an aqueous sucrose solution for 2 hours. Subsequently, the solution was supported on an Al$_2$O$_3$ carrier through incipient-wetness impregnation.

The complex carbonized the coated sucrose through a carbonization process. The carbonization was performed at 300° C. for 3 hours. At this time, the sucrose was attached to the surface of Al$_2$O$_3$ through dehydration between the hydroxyl group and the sucrose on the surface of Al$_2$O$_3$. Subsequently, the sucrose attached to the surface was changed to a polycyclic aromatic carbon sheet after the carbonization process was performed at 300° C. for 3 hours. The carbonization process was performed under a condition that nitrogen flowed at 100 cc/min and a ramping rate was 5° C./min.

In order to support ruthenium and tin on the C—Al$_2$O$_3$ carrier, a ruthenium precursor (RuCl$_3$, Kojima) and a tin precursor (SnCl$_2$, Aldrich) were dissolved in a distilled water solution and supported through co-impregnation of supporting the two precursors at a time. The catalyst supported ruthenium in 5 parts by weight based on 100 parts by weight of the C—Al$_2$O$_3$ carrier. At this time, the amount of the tin was supported in the same number of moles as ruthenium and reduced at 500° C. for 3 hours (100 cc/min H$_2$:30/N$_2$:70), and this was used as a catalyst for a dicarboxylic acid hydrogenation reaction.

Figure 4:
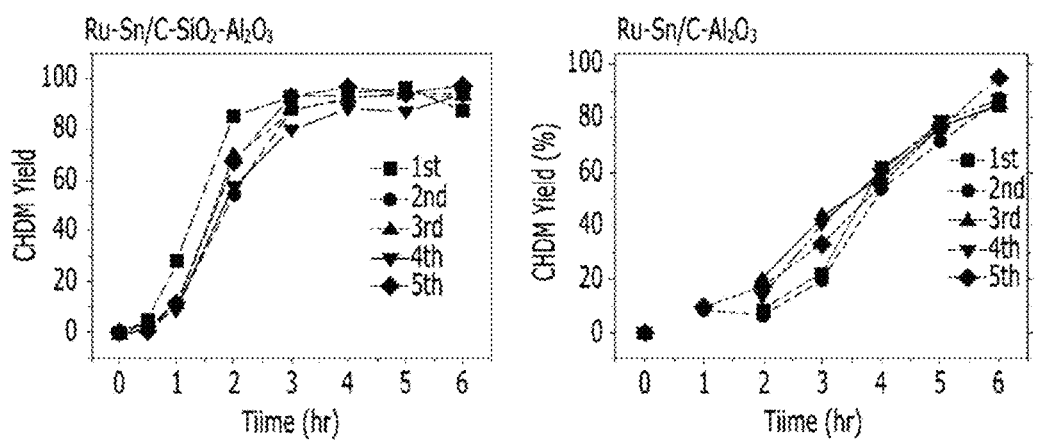
FIG. 4 is graphs showing CHDM production reaction efficiency results using a catalyst in which a noble metal-transition metal is supported on a carbon-coated silica-alumina carrier and a carbon-uncoated silica-alumina carrier, according to an embodiment of the present invention.

In this regard, in order for comparison of the performance and durability with the Ru—Sn/C—SiO$_2$—Al$_2$O$_3$ catalyst applied to Example 3, a heterometal catalyst (Ru—Sn/C—Al$_2$O$_3$) supported on the carbon-coated Al$_2$O$_3$(C—Al$_2$O$_3$) prepared in Comparative Example 2 was applied to the CHDA conversion reaction. The experimental procedure was the same as that in Example 3, and the results of five activities of the respective catalyst are illustrated in FIG. 4 over time so as to compare the reaction rates.

As a result of the reaction, it was confirmed that the Ru—Sn/C—SiO$_2$—Al$_2$O$_3$ catalyst produced the CHDM faster than the Ru—Sn/C—Al$_2$O$_3$ catalyst. It can be seen that the catalyst produces the CHDM more efficiently.

Although the present invention has been described with reference to the drawings according to embodiments of the present invention, it will be understood by those of ordinary skill in the art that various applications and modifications can be made thereto without departing from the scope of the present invention.

The invention claimed is:

1. A noble metal-transition metal complex catalyst supported on a carbon-coated silica-alumina carrier, wherein
    40 parts by weight to 95 parts by weight of alumina (Al$_2$O$_3$) and 5 parts by weight to 60 parts by weight of silica (SiO$_2$) are included based on 100 parts by weight of the carbon-coated silica-alumina carrier; and
    2 parts by weight to 20 parts by weight of the noble metal and the transition metal are included based on 100 parts by weight of the carbon-coated silica-alumina carrier,
    wherein the noble metal includes one or more selected from the group consisting of palladium (Pd), rhodium (Rh), ruthenium (Ru), and platinum (Pt),
    the transition metal includes one or more selected from the group consisting of tin (Sn), iron (Fe), rhenium (Re), and gallium (Ga), and
    an amount of the transition metal is in a range of 1 part by weight to 10 parts by weight based on 100 parts by weight of the carbon-coated silica-alumina carrier.

2. The noble metal-transition metal complex catalyst of claim 1, wherein an amount of the noble metal is in a range of 1 part by weight to 10 parts by weight based on 100 parts by weight of the carbon-coated silica-alumina carrier.

3. The noble metal-transition metal complex catalyst of claim 1, wherein a noble metal precursor and a transition metal precursor are supported on the carbon-coated silica-alumina carrier at the same molar ratio before being reduced with hydrogen.

4. The noble metal-transition metal complex catalyst of claim 1, wherein the carbon is coated on the surface of the silica-alumina through a carbonization process.

5. A hydrogenation method comprising hydrogenating a dicarboxylic acid group in the presence of the catalyst according to claim 1.

6. The hydrogenation method of claim 5, wherein the dicarboxylic acid is one selected from the group consisting of an oxalic acid, a malonic acid, a succinic acid, a glutaric acid, an adipic acid, a pimelic acid, a suberic acid, an azelaic acid, a sebacic acid, a malic acid, an aspartic acid, a glutamic acid, a phthalic acid, an isopthalic acid, a terephthalic acid, and a cyclohexane dicarboxylic acid.

7. A method for preparing the noble metal-transition metal complex catalyst supported on a carbon-coated silica-alumina carrier of claim 1, the method comprising:
    (a) preparing a complex by dissolving a boric acid in an aqueous carbon precursor solution and supporting the resultant mixture on silica-alumina (SiO$_2$—Al$_2$O$_3$);
    (b) carbonizing the complex;

(c) supporting a noble metal-transition metal on a carbon-coated silica-alumina ($SiO_2$—$Al_2O_3$) carrier; and (d) reducing a noble metal-transition metal oxide supported on the silica-alumina ($SiO_2$—$Al_2O_3$) carrier with hydrogen.

8. The method of claim 7, wherein, in the step (a), the carbon precursor and the boric acid are added at a weight ratio of 1:0.005 to 1:0.1.

9. The method of claim 7, wherein, in the step (a), the complex is prepared by being supported on the carrier by incipient-wetness impregnation.

10. The method of claim 7, wherein, in the step (b), the carbonization process is performed in a temperature range of 300° C. to 700° C. in a nitrogen atmosphere.

11. The method of claim 7, wherein, in the step (c), the noble metal and the transition metal are supported in 2 parts by weight to 20 parts by weight based on 100 parts by weight of the carbon-coated silica-alumina carrier.

12. The method of claim 7, wherein, in the step (d), the reduction process is performed in a temperature range of 400° C. to 600° C.

* * * * *